(12) United States Patent
Aferzon et al.

(10) Patent No.: US 10,925,484 B2
(45) Date of Patent: Feb. 23, 2021

(54) INTERPUPILLARY CALIBRATION SYSTEM, APPARATUS, AND METHOD FOR STEREOSCOPIC VISUALIZATION

(71) Applicant: Aferzon Medical, LLC, Avon, CT (US)

(72) Inventors: Joshua Aferzon, Stamford, CT (US); Lee M. Nicholson, Katonah, NY (US)

(73) Assignee: Orthozon Technologies, LLC, Stamford, CT (US)

( * ) Notice: Subject to any disclaimer, the term of this patent is extended or adjusted under 35 U.S.C. 154(b) by 28 days.

(21) Appl. No.: 16/127,756

(22) Filed: Sep. 11, 2018

(65) Prior Publication Data

US 2019/0076013 A1    Mar. 14, 2019

Related U.S. Application Data

(60) Provisional application No. 62/558,953, filed on Sep. 14, 2017.

(51) Int. Cl.
  *G02B 7/12* (2006.01)
  *A61B 3/11* (2006.01)
  (Continued)

(52) U.S. Cl.
  CPC ............ *A61B 3/111* (2013.01); *G02B 27/017* (2013.01); *G02C 13/005* (2013.01);
  (Continued)

(58) Field of Classification Search
  CPC ......... A61B 3/111; A61B 3/0025; A61B 3/11; G02C 13/005; G02C 7/088;
  (Continued)

(56) References Cited

U.S. PATENT DOCUMENTS

| 5,886,822 | A | * | 3/1999 | Spitzer | ............... G02B 27/0172 359/630 |
| 5,926,318 | A | * | 7/1999 | Hebert | ................. G02B 27/017 345/8 |

(Continued)

OTHER PUBLICATIONS

International Search Report and Written Opinion issued in International Application No. PCT/US2018/050422 dated Nov. 8, 2018.

*Primary Examiner* — Balram T Parbadia
(74) *Attorney, Agent, or Firm* — Hoffmann & Baron, LLP

(57) ABSTRACT

Interpupillary calibration system and method for stereoscopic visualization. The system includes a first display, second display, and calibration processor. The first display is disposed in proximity to a left aperture of an eyeframe to present a first image area through the left aperture, the first image area associated with an image and having a first display axis. The second display is disposed in proximity to a right aperture of the eyeframe to present a second image area through the right aperture, the second image area associated with the image and having a second display axis. The calibration processor is configured to adjust a display distance between the first image area and second image area based on an interpupillary distance of a user, wherein the first image area and second image area are visible through the first aperture and second aperture enabling formation of a stereoscopic view of the image.

18 Claims, 9 Drawing Sheets

(51) Int. Cl.
*G02C 13/00* (2006.01)
*H04N 13/327* (2018.01)
*G02B 27/01* (2006.01)
*H04N 13/106* (2018.01)
*H04N 13/194* (2018.01)
*H04N 13/344* (2018.01)
*A61B 3/00* (2006.01)
*H04N 13/20* (2018.01)
*G02C 7/08* (2006.01)
*G02B 27/00* (2006.01)

(52) U.S. Cl.
CPC ......... *H04N 13/106* (2018.05); *H04N 13/194* (2018.05); *H04N 13/327* (2018.05); *H04N 13/344* (2018.05); *A61B 3/0025* (2013.01); *G02B 27/0093* (2013.01); *G02B 2027/0178* (2013.01); *G02C 7/088* (2013.01); *H04N 13/20* (2018.05)

(58) Field of Classification Search
CPC ........ G02B 2027/0129; G02B 27/0093; G02B 27/017; G02B 7/12; G02B 2027/0134; G02B 2027/0178; H04N 13/10; H04N 13/20; H04N 13/239; H04N 13/25; H04N 13/344; H04N 13/366; H04N 13/371; H04N 13/106; H04N 13/194; H04N 13/327

See application file for complete search history.

(56) References Cited

U.S. PATENT DOCUMENTS

| | | | |
|---|---|---|---|
| 6,356,392 B1* | 3/2002 | Spitzer | G02B 27/017 345/8 |
| 8,882,662 B2* | 11/2014 | Charles | A61B 17/0218 600/214 |
| 2012/0280893 A1* | 11/2012 | Holakovszky | G02B 27/017 345/8 |
| 2013/0050833 A1 | 2/2013 | Lewis et al. | |
| 2013/0170031 A1 | 7/2013 | Bohn et al. | |
| 2015/0123880 A1* | 5/2015 | Tam | G02B 25/004 345/8 |
| 2017/0099481 A1 | 4/2017 | Held et al. | |

* cited by examiner

INTERPUPILLARY CALIBRATION SYSTEM, APPARATUS, AND METHOD FOR STEREOSCOPIC VISUALIZATION

CROSS REFERENCE TO RELATED APPLICATIONS

This application claims benefit of U.S. Provisional Patent Application No. 62/558,653, filed on Sep. 14, 2017, the contents of which are incorporated herein by reference in their entirety.

BACKGROUND

Field

The present disclosure relates to stereoscopic visualization. More particularly, the present disclosure is directed to an interpupillary calibration system, apparatus, and method for stereoscopic visualization.

Brief Discussion of Related Art

Interpupillary distance is a distance between centers or optical axes of the pupils of a person's two eyes. This distance determines a plurality of images that are received through the person's eyes and the distinct perspectives of the images that are combined by the person's brain to produce stereoscopic perception or stereopsis. The distances can vary widely in different people based on their age, gender, race, and other factors, such as disease or anomalies that can affect pupil location and orientation. Typically, the interpupillary distance in adults is around 54 mm to 68 mm, and is generally between 48 mm and 73 mm.

Moreover, the interpupillary distance represents an important factor in the design of stereoscopic display systems. These systems can include binocular microscopes, wearable devices, such as night-vision goggles and head-mounted displays, as well as other stereoscopic display systems in a variety of fields. More specifically, the interpupillary distance can be used in the design of such systems and can further be used in determining adjustment between the optical axes available in these systems.

While stereoscopic display systems can be designed with a fixed interpupillary distance that accommodates a range of distances and minimizes the weight, bulk, cost, and delivery time, an adjustable interpupillary distance design could accommodate a range of distances but generally requires prior customization or mechanical adjustment of the stereoscopic display systems in order to align the display properly with the person's interpupillary distance and pupil orientation.

Such mechanical alignment can add significant cost and delivery time, as well as increase significantly the complexity, including weight and bulk, in connection with the design and manufacture of stereoscopic display systems for even the most common visualization applications. While the foregoing factors are not overly critical for large stereoscopic display systems, such as microscopes, these factors are nonetheless increasingly restrictive and problematic for wearable stereoscopic display systems, particularly for surgical applications, such as surgical loupes, in terms of usability and comfort.

It is therefore desirable to provide an interpupillary calibration system, apparatus, and method that, through a series of calibration images and control logic, facilitate the alignment of the calibration images displayed and adjusted for each individual eye of a person based on the person's interpupillary distance, including pupil location and orientation, in order to replicate or enhance the person's natural stereoscopic visualization, even with the person's unusual characteristics that can affect the location and orientation of the person's pupils.

SUMMARY

In accordance with an embodiment, disclosed herein is an interpupillary calibration system for stereoscopic visualization. The interpupillary calibration system includes a first display, a second display, and a calibration processor.

The first display is disposed in proximity to a left aperture of an eyeframe to present a first image area through the left aperture, wherein the first image area is associated with an image and has a first display axis.

The second display is disposed in proximity to a right aperture of the eyeframe to present a second image area through the right aperture, wherein the second image area is associated with the image and having a second display axis.

The calibration processor is configured to adjust a display distance between the first image area and the second image area based on an interpupillary distance of a user, wherein the first image area and the second image area are visible through the first aperture and the second aperture enabling formation of a stereoscopic view of the image.

The system can further include a first controller and a second controller. The first controller circuit can be associated with the first display, wherein the first controller circuit is configured to transmit one or more first signals to the first display to control presentation of the first image area. Similarly, the second controller circuit can be associated with the second display, wherein the second controller circuit is configured to transmit one or more second signals to the second display to control presentation of the second image area.

Moreover, the first controller circuit can include a first electronic display driver that is configured to generate the first signals to control presentation of the first image area on the first display. Similarly, the second controller circuit can include a second electronic display driver configured to generate the second signals to control presentation of the second image area on the second display.

The first controller circuit can further include a first adjustment factor storage configured to store first adjustment factors associated with presentation of the first image area on the first display. Similarly, the second controller circuit can further include a second adjustment factor storage configured to store second adjustment factors associated with presentation of the second image area on the second display.

In view of the foregoing, adjustment of the display distance between the first image area and the second image area can include movement of the first image area presented on the first display, movement of the second image area presented on the second display, or movement of the first image and the second image. The movement of the first image area, the second image area, or first image and the second image can include horizontal movement, vertical movement, or horizontal and vertical movement.

The adjustment of the display distance between the first image area and the second image area can also include size adjustment of the first image area presented on the first display, size adjustment of the second image area presented on the second display, or size adjustment of the first image and the second image. The size adjustment of the first image area, the second image area, or first image and the second image can include horizontal size adjustment, vertical size adjustment, or horizontal and vertical size adjustment.

The system can further include an electronics pack connected to the first controller circuit and the second controller circuit, wherein the electronics pack includes the calibration processor. The calibration processor can generate one or more first commands associated with first signals that control presentation of the first image area and one or more second commands associated with second signals that control presentation of the second image area. The first commands or the second commands are voice inputs or keyboard inputs, or voice inputs and keyboard inputs.

In accordance with an embodiment, disclosed herein is an interpupillary calibration method for stereoscopic visualization. According to the method, a first image area is presented through a left aperture on a first display disposed in proximity to the left aperture of an eyeframe, the first image area being associated with an image and having a first display axis. Moreover, a second image area is presented through a right aperture on a second display disposed in proximity to the right aperture of the eyeframe, the second image area being associated with the image and having a second display axis. Lastly, a display distance between the first image area and the second image area is adjusted based on an interpupillary distance of a user, wherein the first image area and the second image area are visible through the first aperture and the second aperture enabling formation of a stereoscopic view of the image.

The method can further include transmitting one or more first signals from a first controller circuit to the first display to control presentation of the first image area, the first controller circuit being associated with the first display, and transmitting one or more second signals from a second controller circuit to the second display to control presentation of the second image area, the second controller circuit being associated with the second display.

The method can further include generating via a first electronic display driver the first signals to control presentation of the first image area on the first display, wherein the first controller circuit includes the first electronic display driver, and generating via a second electronic display driver the second signals to control presentation of the second image area on the second display, wherein the second controller circuit includes the second electronic display driver.

The method can further include storing first adjustment factors associated with presentation of the first image area on the first display in a first adjustment factor storage, wherein the first controller circuit includes the first adjustment factor storage, and storing second adjustment factors associated with presentation of the second image area on the second display in a second adjustment factor storage, wherein the second controller circuit includes the second adjustment factor storage.

In some cases, the adjustment of the display distance between the first image area and the second image area can include moving the first image area presented on the first display, moving the second image area presented on the second display, or moving the first image and the second image.

The movement of the first image area, the second image area, or first image and the second image can include moving the first image area, moving the second image area, or moving the first image and the second image horizontally, vertically, or horizontal and vertically.

In some cases, the adjustment of the display distance between the first image area and the second image area can include adjusting size of the first image area presented on the first display, adjusting size of the second image area presented on the second display, or adjusting size of the first image and the second image.

The size adjustment of the first image area, the second image area, or first image and the second image can include horizontal size adjustment, vertical size adjustment, or horizontal and vertical size adjustment.

The method can further include generating via a calibration processor one or more first commands associated with first signals that control presentation of the first image area and one or more second commands associated with second signals that control presentation of the second image area, wherein the calibration processor is comprised in an electronics pack that is connected to the first controller circuit and the second controller circuit.

The method can further include inputting the first commands or the second commands, wherein the first commands or the second commands are voice inputs or keyboard inputs, or voice inputs and keyboard inputs.

BRIEF DESCRIPTION OF DRAWINGS

The accompanying drawings are presented to aid in the description of embodiments of the disclosure and are provided solely for illustration of the embodiments and not limitation thereof.

DETAILED DESCRIPTION

Described herein are an interpupillary calibration system, apparatus, and method for enabling stereoscopic visualization. The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

Figure 1A:
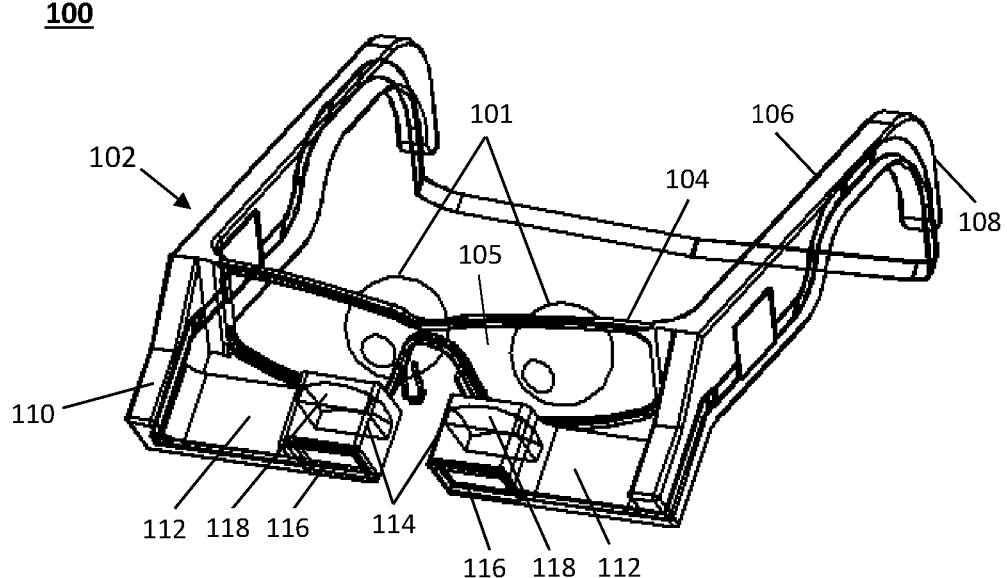
FIG. 1A illustrates a perspective view of an example apparatus 100 that enables interpupillary calibration for stereoscopic visualization.

FIG. 1A illustrates a perspective view of an example apparatus 100 that enables interpupillary calibration for stereoscopic visualization. The display apparatus 100 includes a frame 102, which includes an eye frame 104, earpieces 106, and holders 110. The frame 102 may be made from a material such as a polymer, metal, ceramic, or composites of one or more thereof. Moreover, one or more other materials may be used for the frame 102.

The eye frame 104 can include a plurality of lenses 105 for the purposes of magnifying incoming light waves or interfering with incoming light waves. The eyeframe 104 includes a plurality of apertures (e.g., circular, elliptical, rectangular, another shape, or any combination of shapes that are configured to allow the user (e.g., surgeon) to see individual displays through the apertures of the eyeframe 104, which in combination allow the user to form a stereoscopic view. The apertures of the eyeframe 104 can hold the lenses 105, which can be corrective lenses based on the user's eyesight, magnifying compound lenses, single lenses, symmetric lenses, asymmetric lenses, or combinations thereof.

The earpieces 106 extend from the eye frame 104 to the back of the eye frame 104 and beyond the user's ear, with a hook section 108 configured to secure the frame 102 over the user's face and ears. The earpieces 106 can be formed monolithically with the eye frame 104 (e.g., via injection molding), or can be attached to the eye frame 104 (e.g., via gluing).

The holders 110 extend from the earpieces 106 to the front of the eyeframe 104. The holders 110 can extend in front of and partially below the eyeframe 104, allowing the user to see surrounding external view through the apertures of the eyeframe 104, as well as to see the displays 116 through the apertures of the eyeframe 104.

More specifically, a holder 110 includes an arm 112 and an electronic display housing 114. For example, the holders 110 include arms 112 that extend at the bottom of the holders 110 toward a center of the eyeframe 104, and the electronic display housings 114 that are disposed along terminal portions of the arms 112 extending toward the center of the eyeframe 104, allowing the user to see the surroundings external to the apparatus 100 with greater visibility through the apertures of the eyeframe 104, over arms 112 and the electronic display housings 114.

In some cases, the holders 110 can slope down from the eyeframe 104, which allows the arms 112 and the electronic display housings 114 to be angulated with respect to the eyeframe 104, providing visibility of the surroundings external to the apparatus 100 when the user looks straight through the eyeframe 104, and also providing visibility of the surgical field when the user looks down through the eyeframe 104 into the electronic display housings 106.

An electronic display housing 114 includes an aperture that extends from the back of the housing 114 toward the eyeframe 104, and is configured to house an electronic display 116 and a magnifying lens 118. The electronic displays 116 can provide respective image data to the user's eyes that can be visualized as a three-dimensional image data using the person's natural stereoscopic visualization. While the left and right arm/housing combinations are shown as two separate structures, these structures can also be one monolithic structure that includes an arm extending between the holders 110 and attaching the housings 114.

The electronic display housings 114 rigidly maintain the position of the electronic displays 116 and magnifying lenses 118 with respect to each other and also with respect to the eyeframe 104.

The electronic displays 116, 116 can receive one or more signals or commands from controller circuits 120, 120 (FIGS. 1B and 4) to control image data displayed on the electronic displays 116, 116 to the user's respective eyes 101, 101, e.g., activate and inactivate pixels on the electronic displays 116, 116.

Each of the magnifying lenses 118 of the display apparatus 100 can include one or more magnifying lenses, which in sum can be referenced generally as a magnifying lens. Light from the display device 116 passes through the housing 106 onto the magnifying lens 118. The magnifying lens 118 is disposed adjacently to the electronic display 118 to receive the image data output of the electronic display 116.

As the light travels through the magnifying lens 118, image data are magnified or de-magnified into a resulting image for view by the user. The resulting image (magnified or de-magnified) exits the housing 114 and travels to the user's eyes through the apertures of the eyeframe 104 (e.g., with or without lenses). More specifically, the magnifying lens 118 bends incoming light from the electronic display 116 and forms a magnified image data output for the user's eyes.

More specifically, the resulting image data will appear farther away than the electronic display 116 actually is, which enables the user to resolve the image properly, similarly to prescription eyeglass lenses. The magnifying lens 118 may be composed of an acrylic, glass, crystal, a composite thereof, or other polymers with glass properties. The magnifying lens 118 may further comprise an anti-reflective coating to prevent external light waves from interfering with the transmission of the image data from the electronic displays 116 through the magnifying lens 118.

Figure 1B:
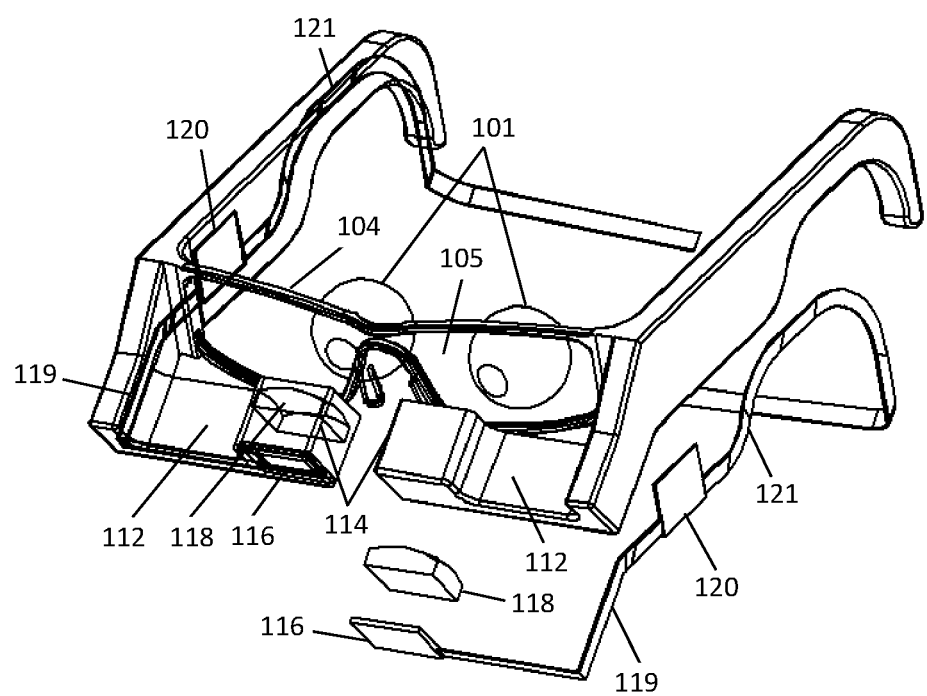
FIG. 1B illustrates an exploded perspective view of the example display apparatus as illustrated in FIG. 1, which enables interpupillary calibration for stereoscopic visualization.

FIG. 1B illustrates an exploded perspective view of the example display apparatus 100 as illustrated in FIG. 1, which enables interpupillary calibration for stereoscopic visualization.

As particularly illustrated in FIG. 1B, data cables 119 connect the electronic displays 116 to respective controller circuits 120. The controller circuits 120 can transmit one or more signals or commands to respective electronic displays 116 in order to control image data that is displayed on these electronic displays 116, e.g., activate and inactivate pixels on the electronic displays 116. The controller circuits 120 are described in greater detail hereinbelow with reference to FIG. 4.

As further illustrated in FIG. 1B, data cables 121 connect the respective controller circuits 120 to an electronics pack 124. The electronics pack 124 is described in greater detail hereinbelow with reference to FIGS. 1C and 2.

Figure 1C:
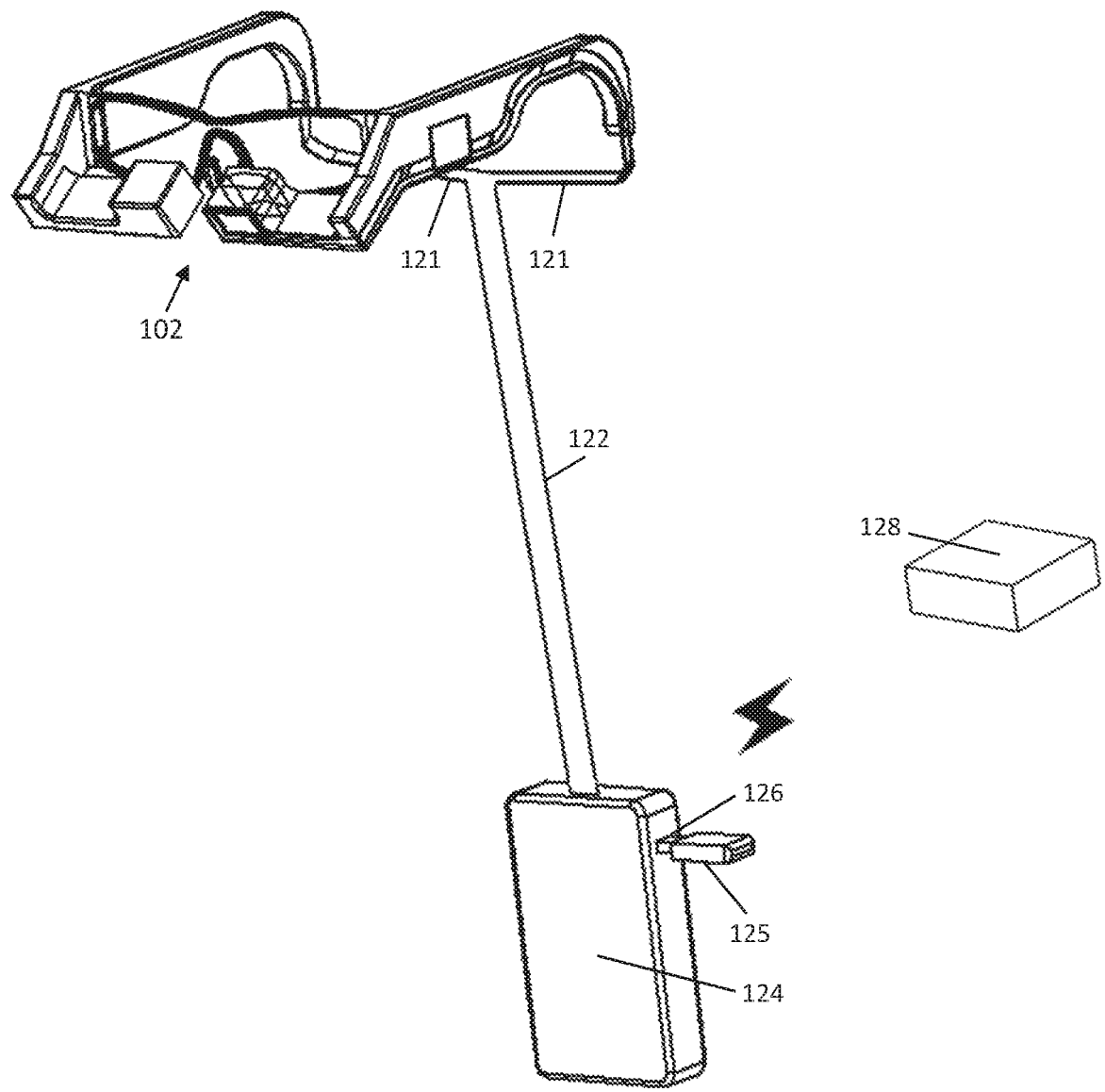
FIG. 1C illustrates a perspective view of an example electronics pack connectable to the display apparatus, enabling interpupillary calibration for stereoscopic visualization.

FIG. 1C illustrates a perspective view of an example electronics pack 124 connectable to the display apparatus 100, enabling interpupillary calibration for stereoscopic visualization.

As particularly illustrated in FIG. 1C, electronics pack 124 is connectable to the display apparatus 100 via data cables 121, which can be enclosed in sheath 122. More specifically, the electronics pack 120 can transmit one or more signals or commands, as well as image data, to the respective controller circuits 120 of the display apparatus 100 in order to control the respective electronic displays 116, e.g., providing and directing display of image data on the electronic displays 116.

The electronics pack 124 can include an external connector 126 that can connect the electronics pack 124 to an external data storage device 125 in order to retrieve stored video, stored images, or custom settings to facilitate interpupillary calibration for stereoscopic visualization. For example, the connector 119 can be a universal serial bus (USB) hub, and the data storage device 125 can be a USB flash drive, or another external storage device (e.g., hard-drive) connectable via a USB data cable.

Moreover, the electronics pack 124 can be connectable to external image data transmitter 128 for stereoscopic visualization using display apparatus 100 after interpupillary calibration. The connection to external image data transmitter 128 can be wired (e.g., via connector 126) or can be wireless (e.g., via wireless data receiver 134 of FIG. 2). The image data from the external image data transmitter 128 can include image data from a plurality of cameras, a video storage unit, a screen monitor, a computer, or a video processor.

Figure 2:
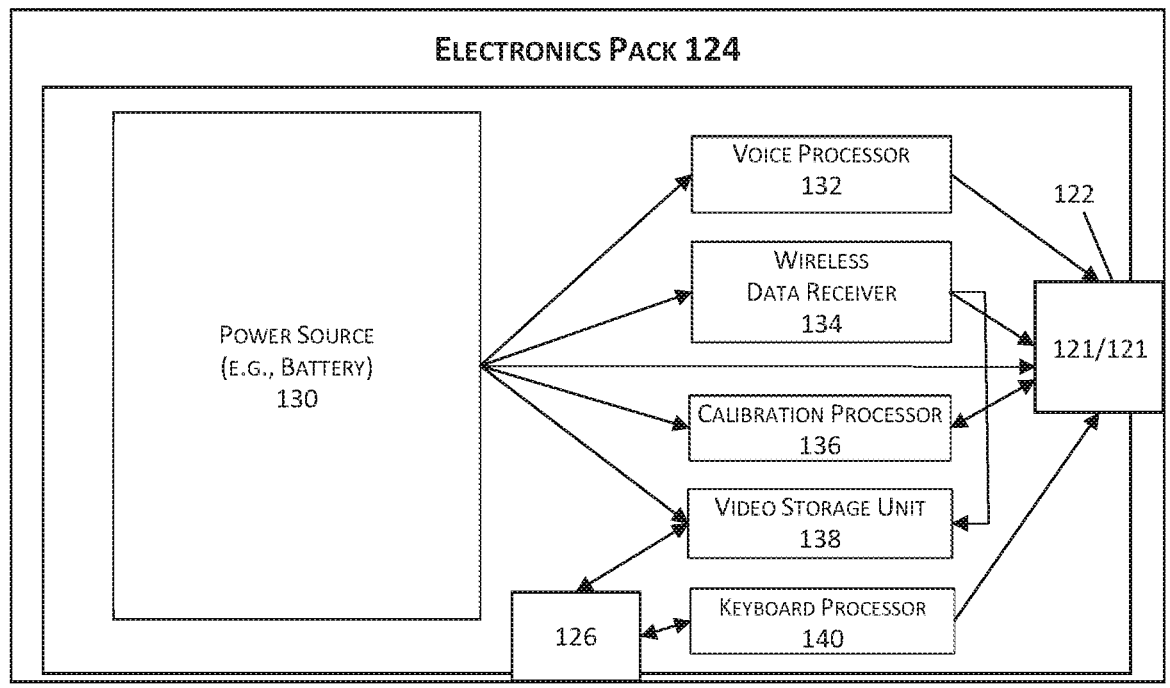
FIG. 2 illustrates a schematic view of the electronics pack as illustrated in FIG. 2.

FIG. 2 illustrates a schematic view of the electronics pack 124. The electronics pack 124 includes a power source 130, voice processor 132, wireless data receiver 134, calibration processor 136, video storage unit 138, and keyboard processor 140.

The power source 130 can be a battery, which can include a lithium-ion battery, zinc-carbon battery, alkaline battery, nickel-cadmium battery, nickel-zinc battery, nickel metal hydride battery, an electric current supply, and one or more combinations thereof.

Moreover, the power source 130 can deliver power to the voice processor 132, wireless data receiver 134, calibration processor 136, video storage unit 138 and keyboard processor 140. The power source 130 can also supply power to the respective controller circuits 120 and electronic displays 116 through the data cables 121, 121.

The voice processor 130 can process voice inputs received from the voice controller 308 of the controller circuit 120 (FIG. 4) in order to determine one or more control signals or commands from a user.

The wireless data receiver 134 can receive and transmit image data that is received from the external image data transmitter 128, such as from cameras. After receipt of image data, wireless data receiver 134 can transmit the image data to video storage unit 138, which can store the image data for later use.

Moreover, the wireless receiver 134 can also transmit the image data to respective controller circuit 120 to display image data on the electronic display 116. The external connector 126 can establish a direct connection to video storage unit 138 so that the stored image data can be retrieved from the electronics pack 124.

Figure 6:
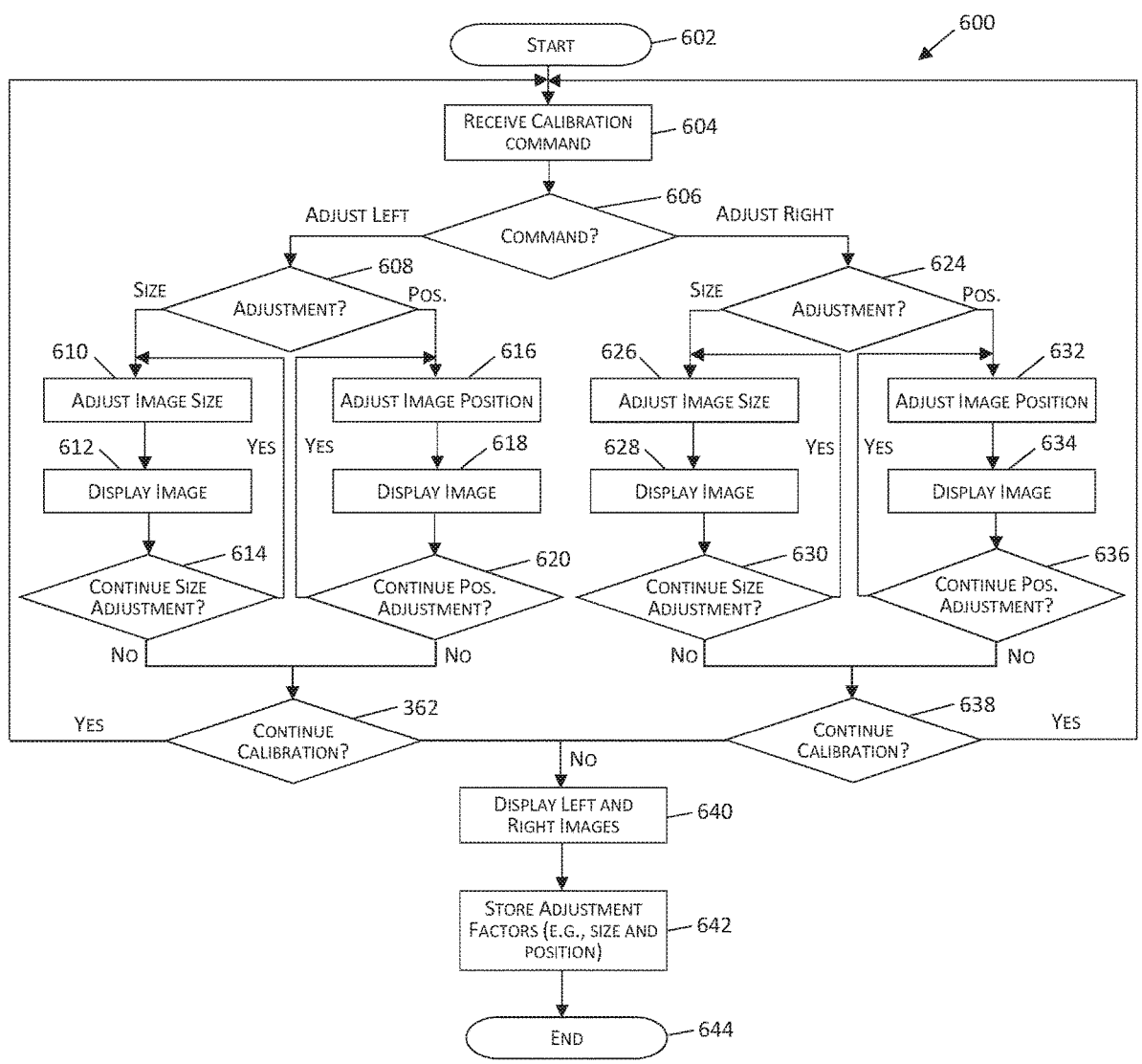
FIG. 6 illustrates a flowchart of an example calibration method for calibrating the display apparatus using calibration images as illustrated in FIGS. 5A and 5B.

The calibration processor 136 can communicate with respective controller circuits 120 and can generate signals or commands that control the displays of the electronic displays 116 to provide interpupillary calibration, for example in accordance with an example calibration method described herein in greater detail in view of FIG. 6.

The keyboard processor 140 can receive keyboard inputs from a keyboard (not shown), which can be connected to the external connector 126. The keyboard processor 140 can then transmit the keyboard inputs to the calibration processor 136, which can translate these keyboard inputs into signals and/or commands to provide interpupillary calibration, for example, in accordance with the example calibration method in view of FIG. 6.

Figure 3A:
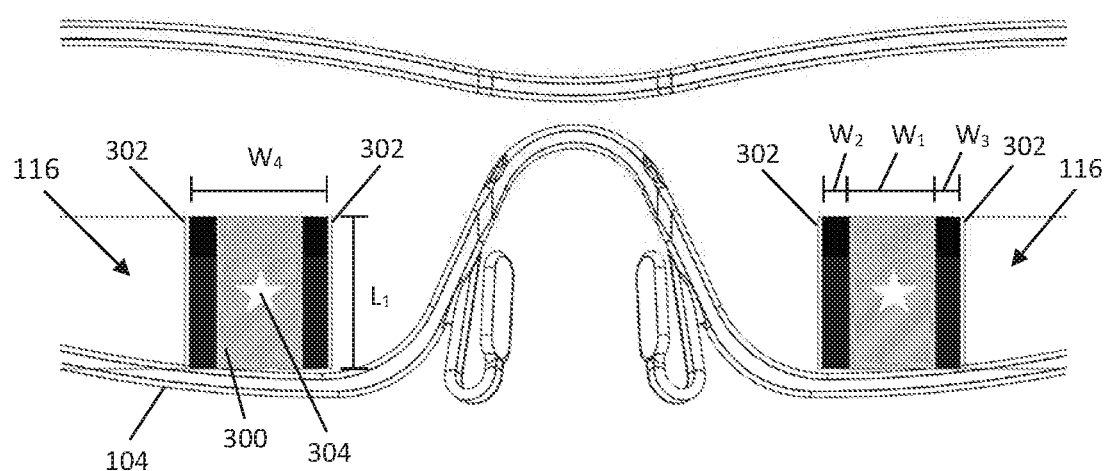
FIG. 3A illustrates a close-up view of electronic displays which display image data to facilitate interpupillary calibration.

FIG. 3A illustrates a close-up view of electronic displays 116 which display image data to facilitate interpupillary calibration.

As illustrated in FIG. 3A, each of the electronic displays 116 includes an image pixel area (or image area) 300 and plurality of peripheral pixel areas (or peripheral areas) 302. While only left and right peripheral pixel areas 302 are illustrated, it should be noted that top and bottom peripheral areas can also be provided and applied based on the description set forth herein.

Each of the electronic displays 116 includes a plurality of pixels that are arranged in an array with a cumulative horizontal dimension $W_4$ and a vertical dimension $L_1$. Individual pixels of the displays 116 can be activated to emit visible light via signals and/or commands delivered from the controller circuit 120 via data cables 119, or can be inactivated via signals and/or commands delivered from the controller circuit 120 and thus remain dark.

The visible light spectrum can also represent various representations of image sensors to the user. As an example, if the image data supplied to the electronics pack 124 from the data transmitter 128 is a heat-map representation of a heat sensor, then the electronic display 116 will display a visible light representation of a heat-map. The frequencies of light from image sensors can include radio, microwave, infrared, visible spectrum, ultraviolet, x-ray, gamma ray, or combinations thereof.

Instead of being inactivated, the peripheral pixel areas 302 can also be activated. More specifically, the peripheral pixel areas 302 can be activated with a solid ambient color space to achieve a similar effect where the human eyes of a user can ignore everything in the ambient color space that is outside of the user's natural field of view.

According to one example, the pixels within the image pixel area 300 are activated to display an object 304, while the pixels in the peripheral pixel areas 302 are left inactivated. The pixels in the image pixel area 300 have a cumulative image horizontal dimension $W_1$, and the pixels in the peripheral pixel areas 302 have a first peripheral horizontal dimension $W_2$ and a second peripheral horizontal dimension $W_3$, where a summation of $W_1+W_2+W_3$ is equal to $W_4$, which is the cumulative horizontal dimension of the electronic display 116.

While only left and right peripheral pixel areas 302 are illustrated in FIG. 3A, it should be noted that top and bottom peripheral areas can also be provided by subdividing the vertical dimension similarly into $L_1$, $L_2$, $L_3$ that can be summated to $L_4$, which would then be the cumulative vertical dimension of the electronic display 116.

Figure 3B:
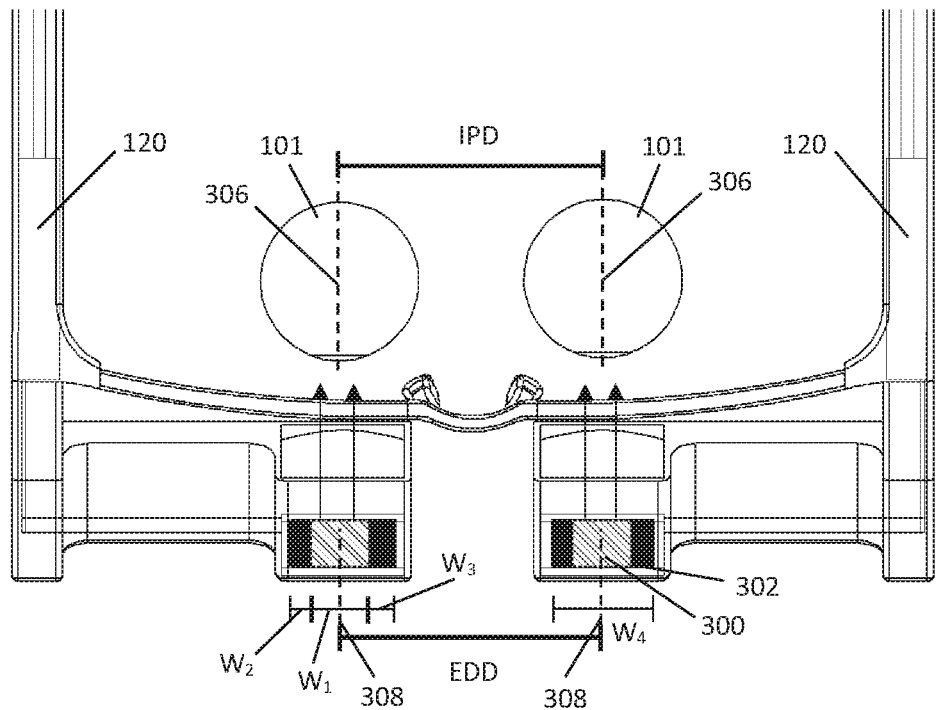
FIGS. 3B and 3C illustrate a top view of the display apparatus with a pair of human eyes of the user that have an intra-pupillary distance.
Figure 3C:
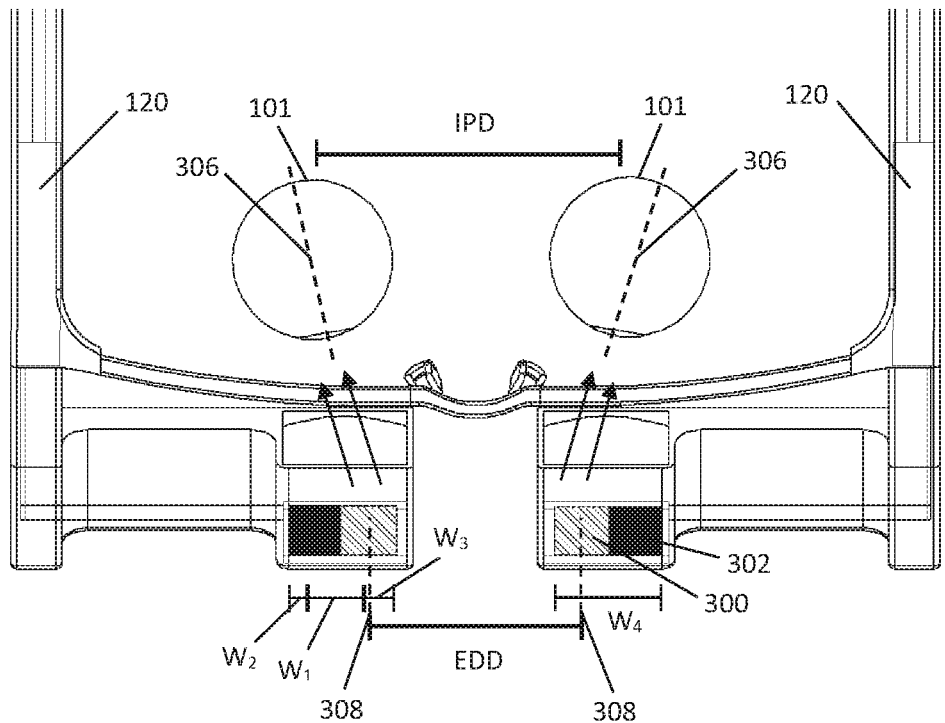

FIGS. 3B and 3C illustrate a top view of a display apparatus 100 with a pair of human eyes 101, 101 of the user that have an intra-pupillary distance IPD. It should be noted that the intra-pupillary distance IPD of the user is fixed.

As illustrated in FIG. 3B, the activated image pixel areas 300 are located at certain positions along the electronic displays 116, 116 such that the pupil central axes 306, 306 of the user's eyes 101, 101 approximately intersect the display central axes 308, 308 of the respective electronic displays 116, 116. As particularly illustrated, the electronic displays 116, 116 are separated by an electronic display distance EDD, which also represents a distance between intersection points of the pupil central axes 306, 306 and the display central axes 308, 308 in front of the user's eyes 101, 101. The electronic display distance EDD can include adjustments for unique characteristics of the user's eyes 101, 101, including but not limited to shape, size, viewing angle, strabismus, and/or other characteristics of the user's eyes 101, 101.

As illustrated in FIG. 3C, the display central axes 308, 308 of the electronic displays 116 are offset horizontally in relation with respect to the pupil central axes 306, 306 of the user's eyes 101, 101, such that the electronic display distance EDD is adjusted to account for certain unique characteristics of the user's eyes 101, 101 with pupil central axes 306, 306 extending inwardly. It should be noted that the display central axes 308, 308 can be individually offset to various amounts based on the angulation of user pupil central axes 306, 306.

Figure 3D:
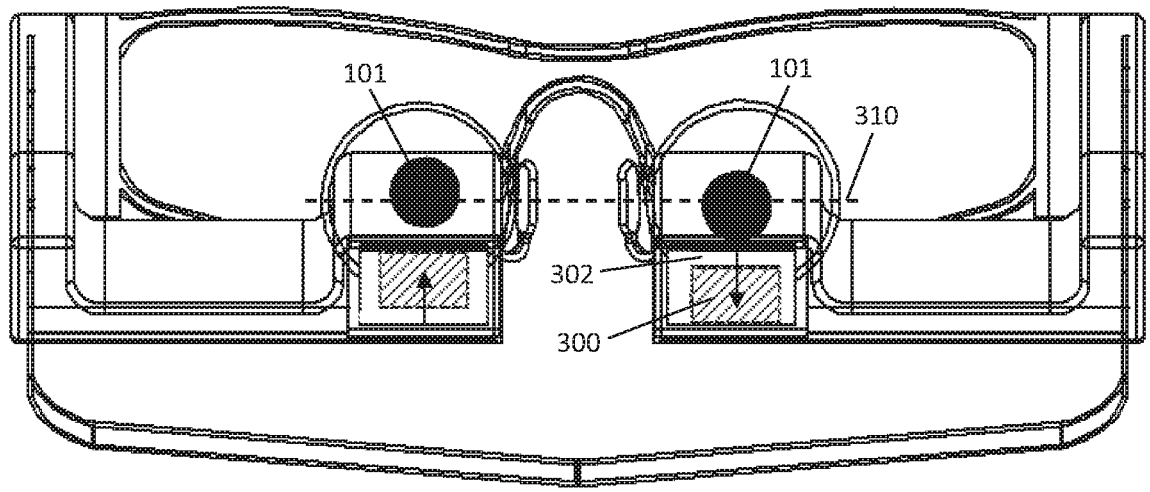
FIG. 3D illustrates a front view of a display apparatus with a pair of human eyes of the user with the pupil central axes at various angulation with respect to a horizontal plane.

FIG. 3D illustrates a front view of a display apparatus 100 with a pair of human eyes 101, 101 of the user with the pupil central axes 306, 306 at various angulations with respect to a horizontal plane 310.

As illustrated in FIG. 3D, the display central axes 308, 308 of the electronic displays 116 are offset vertically in relation to the horizontal plane 310 with respect to the pupil central axes 306, 306 of the user's eyes 101, such that the second intra-pupillary distance $ID_2$ is adjusted to account for certain unique characteristics of the user's eyes 101 with pupil central axes 306, 306 extending at different levels with respect to the horizontal plane 310. It should be noted that the display central axes 308, 308 can be individually offset to various amounts based on the angulation of user pupil central axes 306, 306.

As already described hereinabove, inactivated peripheral pixel areas 302 of the electronic displays 116 do not transmit any light waves to the human eyes 101 for the purposes of isolating and distinguishing the image pixel areas 300 for the user. Similarly, solid ambient-color peripheral pixel areas 302 can achieve a similar effect where the human eyes 101 can ignore everything in the ambient color space that is outside of the natural field of view. The foregoing inactivation or solid ambient color activation can be especially useful for presenting stereoscopic images on the image pixel area 300. More specifically, stereopsis is most comfortable to the user when the left and right images are presented as perfect reflections with an equal and opposite perspective angle.

Figure 4:
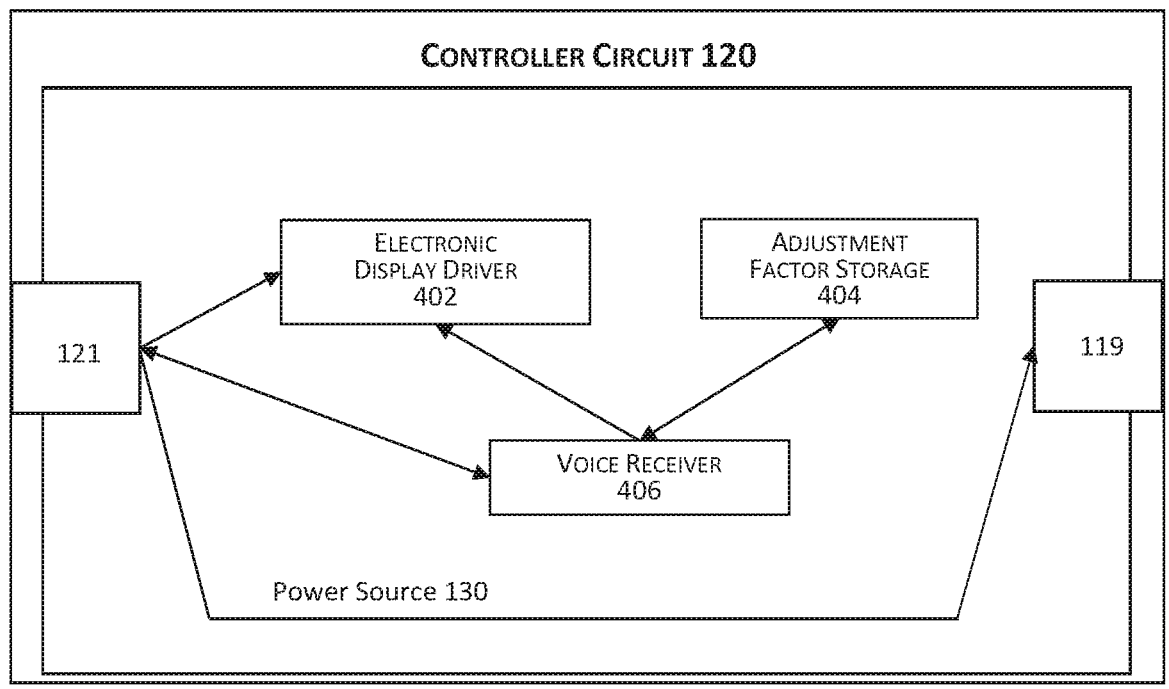
FIG. 4 illustrates a schematic view of a controller circuit as illustrated in FIG. 2.

FIG. 4 illustrates a schematic view of a controller circuit 120 as illustrated in FIG. 2.

The controller circuit 120 includes an electronic display driver 402, an adjustment factor storage 404, and a voice receiver 406, with the power of power source 130 being transmitted through the data cables 121, 119 to the electronic displays 116.

The electronic display driver 402 controls the pixels on the electronic display 116, with the data cables 119 acting as a signal medium to the electronic displays 116.

The adjustment factor storage 404 stores adjustment factors for a user, which can generate image pixel areas 300 on respective electronic displays 116 to achieve comfortable stereopsis for the user.

The voice receiver 406 can receive sound generated by the user and can translate certain sounds into signals and/or commands that are then transmitted to the calibration processor 136, or can transmit sound generated by the user to the voice processor 132, which can translate certain sounds into signals and/or commands that are then transmitted to the calibration processor 136.

In operation, if the display apparatus 100 is turned on and thus receiving power, the electronic display driver 402 can initiate calibration automatically, such as by signaling or commanding the calibration processor 136, when the calibration for the user is performed for the first time. Alternatively, the electronic display driver 402 can retrieve adjustment factors, if available for the user, such as from adjustment factor storage 404, for image pixel areas 300 and automatically illuminate the pixels of the image pixel areas 300 based on the adjustment factors on the electronic displays 116.

The user can also verbally announce to "restart calibration". In this case, the automated retrieval of user's adjustment factors from the adjustment factor storage 404 is overridden and the calibration re-initiated with the electronic display driver 402 signaling or commanding the calibration processor 136 to start calibration. After calibration is completed, the electronic display driver 402 will continue to automatically retrieve the adjustment factors for the user stored in the adjustment factor storage 404 in order to minimize alignment downtime and thereby enhance usability of the display apparatus 100. This can be especially useful when a user is performing critical functions and requires maximum efficiency, such as operating on a patient.

Figure 5A:
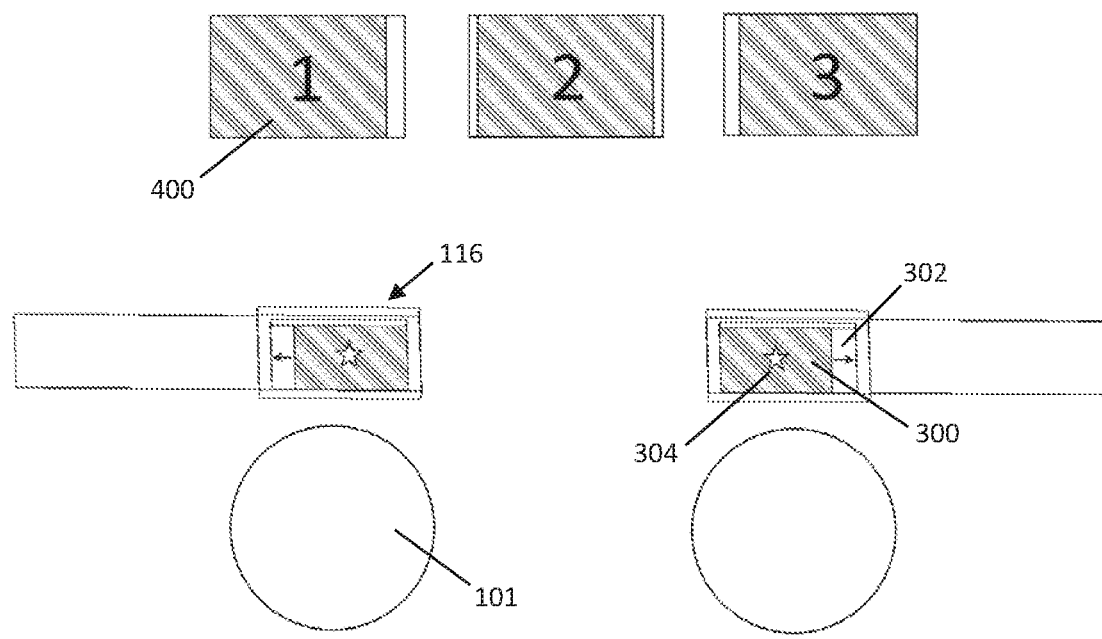
FIGS. 5A and 5B illustrate a series of calibration images that can be adjusted horizontally, vertically, and/or diagonally in order to change their display on electronic displays of the display apparatus to a pair of human eyes of the user.

FIG. 5A illustrates a series of calibration images 400 shown on electronic displays 116 to a pair of eyes 101 of a user. The calibration image data or simply images 400 are a plurality of sequential images that are presented to the user's eyes 112 on the image pixel areas 300 while varying first peripheral horizontal dimensions $W_2$ and second peripheral horizontal dimensions $W_3$ in order to identify comfortable stereoscopic viewing adjustment factors, which are predominantly influenced by intra-pupillary distance.

The calibration images 400 can be adjusted based on pupil location with regard to a shared horizontal access so that the user can appreciate a good stereoscopic view even with unusual characteristics. This includes the adjustment of the calibration images 400 for horizontal displacement, vertical displacement, image size, image resolution, and other properties, in order to accommodate unique characteristics of one or both eyes of the user. The user can thus identify adjustment factors for a comfortable horizontal and vertical displacement for each of the eyes 101, such as by registering the user's preference as to image pixel areas 300 through signals and/or commands received and processed by the controller circuit 120.

Figure 5B:
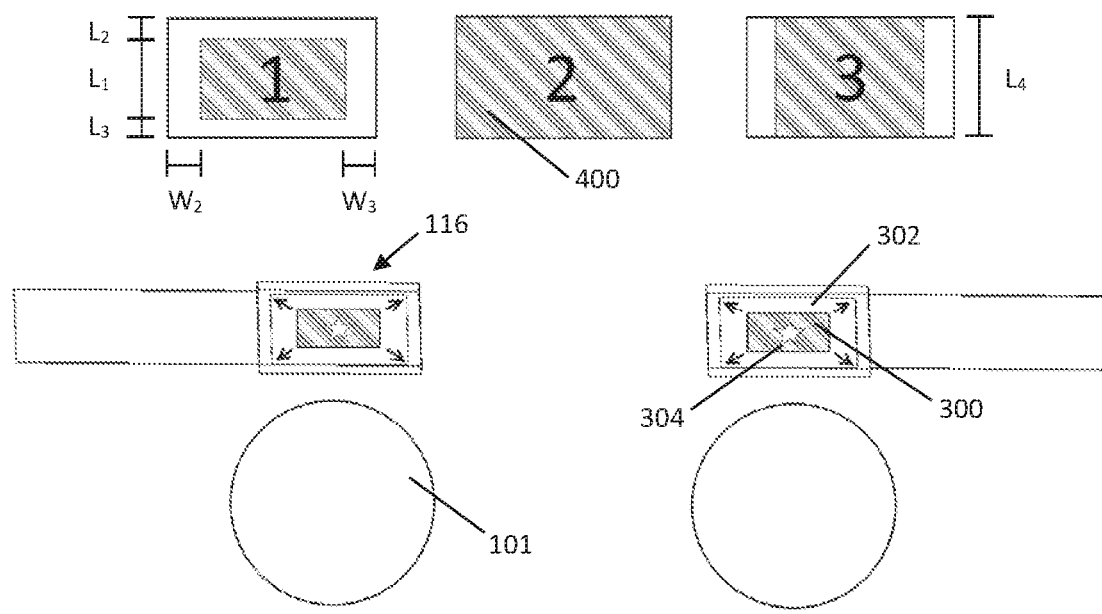

FIG. 5B illustrates a series of calibration images 400 that can be adjusted horizontally, vertically, and/or diagonally in order to change image size and resolution.

The calibration images 400 are a plurality of sequential images that are presented to the eyes 101, 101 of the user on the image pixel areas 300, with variable first peripheral vertical dimension $L_1$, second peripheral vertical dimensions $L_2$, and variable first peripheral horizontal dimensions $W_2$ and second peripheral horizontal dimensions $W_3$.

The first peripheral vertical dimension $L_1$ can be changed to a second peripheral vertical dimension $L_2$, or vice versa, by activating fewer pixels or more pixels, and adjusting the calibration image to occupy a pixel area vertically, horizontally, or proportionally based on $L_2$. This can be useful for accommodating larger or expanded pupil characteristics for certain users. In some cases, the electronic displays 116 can be adjusted to the different $L_2$ dimensions to accommodate unusual discrepancies between the user's eyes 101, 101. In other cases, the first peripheral vertical dimensions $L_1$, second peripheral vertical dimensions $L_2$, first peripheral horizontal dimensions $W_2$, and second peripheral horizontal dimensions $W_3$ can be increased or decreased simultaneously for diagonal proportionality that changes image resolution of the calibration image.

FIG. 6 illustrates a flowchart of an example calibration method 600 for calibrating the display apparatus 100. The calibration method 600 can be executed by the calibration processor 136. It is to be noted that the calibration method 600 can be performed based on user input, via either voice, keyboard, or another input device.

The calibration method 600 starts at operation 602, such as when the display apparatus 100 is turned on for the first time, or user requests calibration. At this time, left and right calibration images are presented on left and right electronic displays 116. At operation 604, a calibration command is received. The calibration command can include a tuple of a command type, adjustment type, and adjustment factor.

At operation 606, a determination is made as to the type of calibration command. If it is determined that the command is to adjust the left calibration image, the method 600 continues at operation 608, and if it is determined that the command is to adjust the right calibration image, the method 600 continues at operation 624.

At operation 608, a determination is made as to the type of adjustment of the left calibration image. If it is determined that the adjustment type is to adjust size of the left calibration image, the method 600 continues at operation 610, and if it is determined that the adjustment type is to adjust the position of the left calibration image, the method 600 continues at operation 616.

At operation 610, the size of the left calibration image is adjusted according to the adjustment factor, and then at operation 612, the left calibration image is displayed on the electronic display 116 based on the adjusted size. At operation 614, a determination is made as to whether the size adjustment should continue, which can be accomplished by receiving a further user input, such as a size adjustment factor or a stop input. If continuation of size adjustment is desired, the method 600 continues at operation 610 to further adjust the size of the left calibration image. If not, the method 600 continues at operation 622, which will be described hereinafter in greater detail.

At operation 616, the position of the left calibration image is adjusted according to the adjustment factor, and then at operation 618, the left calibration image is displayed on the electronic display 116 based on the adjusted position. At operation 620, a determination is made as to whether the position adjustment should continue, which can be accomplished by receiving a further user input, such as a position adjustment factor or a position stop. If continuation of position adjustment is desired, the method 600 continues at operation 610 to further adjust the position of the left calibration image. If not, the method 600 continues at operation 622, as will be described hereinafter.

At operation 622, a determination is made as to whether calibration should be continued. If calibration is to be continued, the method 600 continues at operation 604 to receive another calibration command, e.g., calibration command tuple including a command type, adjustment type, and adjustment factor. If not, the method continues at operation 640, which will be described hereinafter in greater detail.

At operation 624, a determination is made as to the type of adjustment of the right calibration image. If it is determined that the adjustment type is to adjust size of the right calibration image, the method 600 continues at operation 626, and if it is determined that the adjustment type is to adjust the position of the right calibration image, the method 600 continues at operation 632.

At operation 626, the size of the right calibration image is adjusted according to the adjustment factor, and then at operation 628, the right calibration image is displayed on the electronic display 116 based on the adjusted size. At operation 630, a determination is made as to whether the size adjustment should continue, which can be accomplished by receiving a further user input, such as a size adjustment factor or a stop input. If continuation of size adjustment is desired, the method 600 continues at operation 626 to further adjust the size of the right calibration image. If not, the method 600 continues at operation 622, which will be described hereinafter in greater detail.

At operation 632, the position of the right calibration image is adjusted according to the adjustment factor, and then at operation 634, the right calibration image is displayed on the electronic display 116 based on the adjusted position. At operation 636, a determination is made as to whether the position adjustment should continue, which can be accomplished by receiving a further user input, such as a position adjustment factor or a position stop. If continuation of position adjustment is desired, the method 600 continues at operation 632 to further adjust the position of the right calibration image. If not, the method 600 continues at operation 622, as will be described hereinafter.

At operation 638, a determination is made as to whether calibration should be continued. If calibration is to be continued, the method 600 continues at operation 604 to receive another calibration command, e.g., calibration command tuple including a command type, adjustment type, and adjustment factor. If not, the method continues at operation 640, which will be described hereinafter.

At operation 640, the left and right calibration images are finally displayed on the respective electronic displays 116. At this time, the size and positioning of the respective calibration images should be such that the user can form a comfortable stereoscopic image based on the adjusted calibration images. At operation 642, the respective adjustment factors for the left electronic display 116 and the right electronic display are stored, such as in adjustment factor storage 404. The stored adjustment factors can thus be used to adjust left and right image data received from cameras during a surgical procedure, so that the use can form a comfortable stereoscopic image. The calibration method 600 ends at operation 644.

Figure 7:
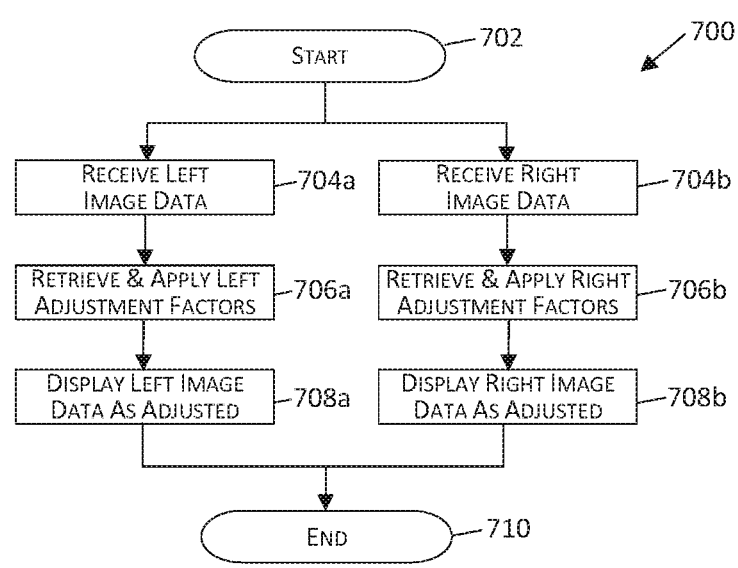
FIG. 7 illustrates a flowchart of an example method that facilitates application of adjustment factors resulting from interpupillary calibration to received respective image data in stereoscopic visualization, such as during a surgical procedure.

FIG. 7 illustrates a flowchart of an example method 700 that facilitates application of the adjustment factors resulting from interpupillary calibration to received respective image data in stereoscopic visualization, such as during a surgical procedure.

At operations 702, the display apparatus 100 is turned on and thus receives power. At operations 704a, 704b, left and right image data can be received from the external image data transmitter 128, which can include image data from a plurality of cameras that can be disposed in a retractor device of a surgical incision.

At operations 706a, 706b, the electronic display driver 402 can retrieve the adjustment factors from adjustment factor storage 404 for the respective left and right image data, and adjust the received respective image data based on the retrieved adjustment factors.

Thereafter, at operations 708a, 708b, the electronic display driver 402 can display the respective left and right image data as adjusted via electronic display 116, e.g., illuminating image pixel areas of the electronic displays 116 based on the adjustment factors.

Figure 8:
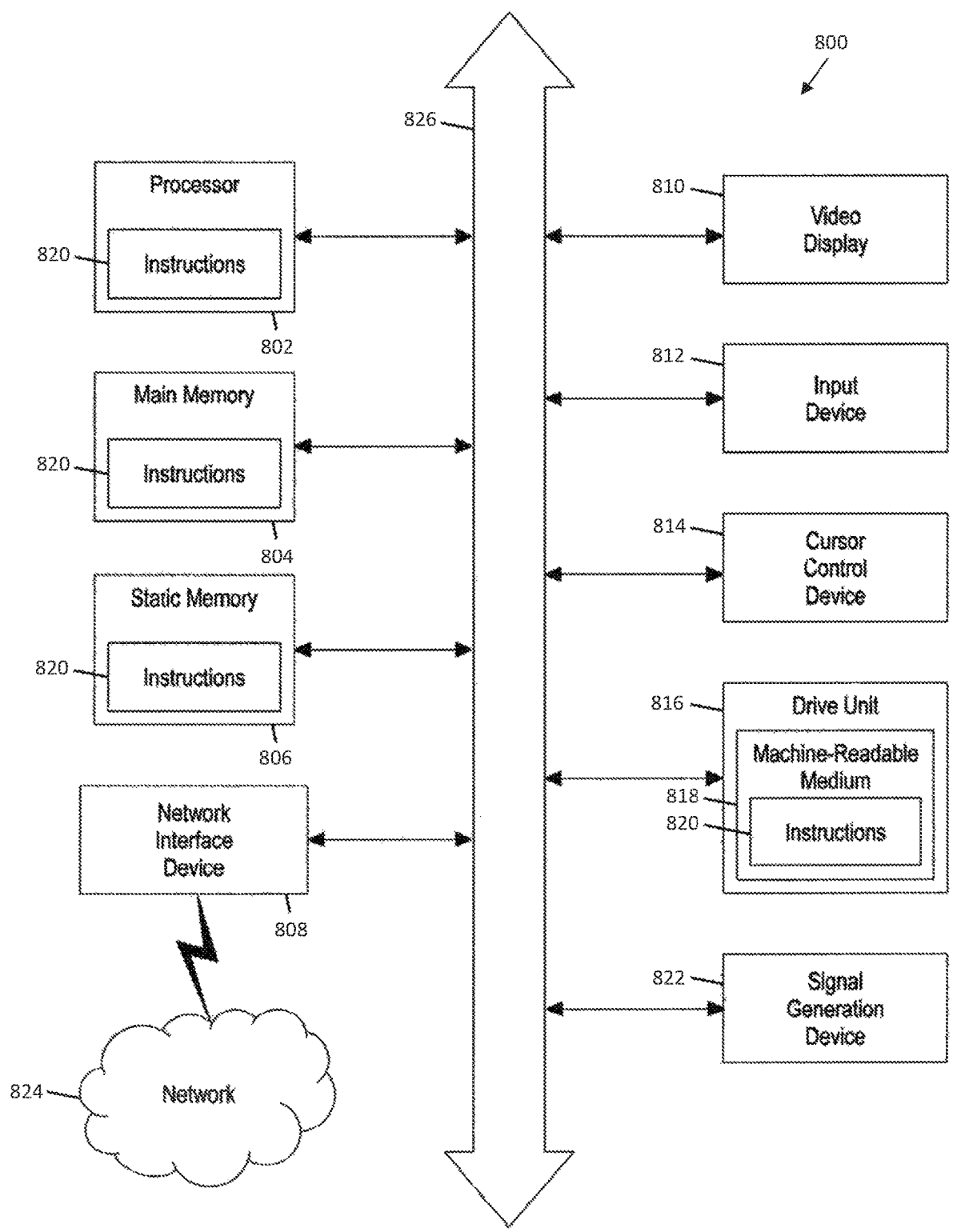
FIG. 8 is a block diagram of an example general computer system.

FIG. 8 is a block diagram of an example general computer system 800. The computer system 1300 can include a set of instructions that can be executed to cause the computer system 800 to perform any one or more of the methods or computer-based functions as disclosed herein in FIGS. 1A-7. The computer system 800, or any portion thereof, may operate as a standalone device or may be connected, e.g., using a network or other connection, to other computer systems or peripheral devices. For example, the computer system 800 may be the electronics pack 124 or external image data transmitter 128, and may further be connected to other systems and devices, such as other computing system(s) via a network.

The computer system 800 may also be implemented as or incorporated into various devices, such as a personal computer (PC), a tablet PC, a personal digital assistant (PDA), a mobile device (e.g., smartphone), a palmtop computer, a laptop computer, a desktop computer, a communications device, a control system, a web appliance, or any other machine capable of executing a set of instructions (sequentially or otherwise) that specify actions to be taken by that machine. Further, while a single computer system 800 is illustrated, the term "system" shall also be taken to include any collection of systems or sub-systems that individually or jointly execute a set, or multiple sets, of instructions to perform one or more computer functions.

As illustrated in FIG. 8, the computer system 800 may include a processor 802, e.g., a central processing unit (CPU), a graphics-processing unit (GPU), or both. Moreover, the computer system 800 may include a main memory 804 and a static memory 806 that can communicate with each other via a bus 826. As shown, the computer system 800 may further include a video display unit 810, such as a liquid crystal display (LCD), an organic light emitting diode (OLED), a flat panel display, a solid state display, or a cathode ray tube (CRT). Additionally, the computer system 800 may include an input device 812, such as a keyboard, and a cursor control device 814, such as a mouse. The computer system 800 can also include a disk drive (or solid state) unit 816, a signal generation device 822, such as a speaker or remote control, and a network interface device 808.

In a particular embodiment or aspect, as depicted in FIG. 8, the disk drive (or solid state) unit 816 may include a computer-readable medium 818 in which one or more sets of instructions 820, e.g., software, can be embedded. Further, the instructions 820 may embody one or more of the methods or logic as described herein. In a particular embodiment or aspect, the instructions 820 may reside completely, or at least partially, within the main memory 804, the static memory 806, and/or within the processor 802 during execution by the computer system 800. The main memory 804 and the processor 802 also may include computer-readable media.

In an alternative embodiment or aspect, dedicated hardware implementations, such as application specific integrated circuits, programmable logic arrays and other hardware devices, can be constructed to implement one or more of the methods described herein. Applications that may include the apparatus and systems of various embodiments or aspects can broadly include a variety of electronic and computer systems. One or more embodiments or aspects described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments or aspects, the methods described herein may be implemented by software programs tangibly embodied in a processor-readable medium and may be executed by a processor. Further, in an exemplary, non-limited embodiment or aspect, implementations can include distributed processing, component/object distributed processing, and parallel processing. Alternatively, virtual computer system processing can be constructed to implement one or more of the methods or functionality as described herein.

It is also contemplated that a computer-readable medium includes instructions 820 or receives and executes instructions 820 responsive to a propagated signal, so that a device connected to a network 824 can communicate voice, video or data over the network 824. Further, the instructions 820 may be transmitted or received over the network 824 via the network interface device 808.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment or aspect, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments or aspects, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile)

memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Although specific example embodiments or aspects have been described, it will be evident that various modifications and changes may be made to these embodiments or aspects without departing from the broader scope of the invention. Accordingly, the specification and drawings are to be regarded in an illustrative rather than a restrictive sense. The accompanying drawings that form a part hereof, show by way of illustration, and not of limitation, specific embodiments or aspects in which the subject matter may be practiced. The embodiments or aspects illustrated are described in sufficient detail to enable those skilled in the art to practice the teachings disclosed herein. Other embodiments or aspects may be utilized and derived therefrom, such that structural and logical substitutions and changes may be made without departing from the scope of this disclosure. This Detailed Description, therefore, is not to be taken in a limiting sense, and the scope of various embodiments or aspects is defined only by the appended claims, along with the full range of equivalents to which such claims are entitled.

Such embodiments or aspects of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or aspects have been illustrated and described herein, it should be appreciated that any arrangement calculated to achieve the same purpose may be substituted for the specific embodiments or aspects shown. This disclosure is intended to cover any and all adaptations or variations of various embodiments or aspects. Combinations of the above embodiments or aspects, and other embodiments or aspects not specifically described herein, will be apparent to those of skill in the art upon reviewing the above description.

The Abstract is provided to comply with 37 C.F.R. § 1.72(b) and will allow the reader to quickly ascertain the nature and gist of the technical disclosure. It is submitted with the understanding that it will not be used to interpret or limit the scope or meaning of the claims.

In the foregoing description of the embodiments or aspects, various features are grouped together in a single embodiment for the purpose of streamlining the disclosure. This method of disclosure is not to be interpreted as reflecting that the claimed embodiments or aspects have more features than are expressly recited in each claim. Rather, as the following claims reflect, inventive subject matter lies in less than all features of a single disclosed embodiment or aspect. Thus, the following claims are hereby incorporated into the Detailed Description, with each claim standing on its own as a separate example embodiment or aspect. It is contemplated that various embodiments or aspects described herein can be combined or grouped in different combinations that are not expressly noted in the Detailed Description.

The invention claimed is:

1. An interpupillary calibration system for stereoscopic visualization, the interpupillary calibration system comprising:
   a first display disposed in proximity to a left aperture of an eyeframe to present a first image area at a first position on the first display through the left aperture, the first image area associated with an image and having a first display axis;
   a second display disposed in proximity to a right aperture of the eyeframe to present a second image area at a second position on the second display through the right aperture, the second image area associated with the image and having a second display axis; and
   a calibration processor configured to adjust a display distance between the first image area and the second image area based on an interpupillary distance of a user via movement of the presentation of the first image area to a third position on the first display, movement of the presentation of the second image area to a fourth position on the second display, or movement of the first image area and the second image area respectively to the third position and the fourth position, wherein the first image area and the second image area are visible through the first aperture and the second aperture enabling formation of a stereoscopic view of the image.

2. The interpupillary calibration system of claim 1, wherein the system further comprises:
   a first controller circuit associated with the first display, the first controller circuit configured to transmit one or more first signals to the first display to control presentation of the first image area; and
   a second controller circuit associated with the second display, the second controller circuit configured to transmit one or more second signals to the second display to control presentation of the second image area.

3. The interpupillary calibration system of claim 2, wherein:
   the first controller circuit comprises a first electronic display driver configured to generate the first signals to control presentation of the first image area on the first display; and
   the second controller circuit comprises a second electronic display driver configured to generate the second signals to control presentation of the second image area on the second display.

4. The interpupillary calibration system of claim 3, wherein:
   the first controller circuit further comprises a first adjustment factor storage configured to store first adjustment factors associated with presentation of the first image area on the first display; and
   the second controller circuit further comprises a second adjustment factor storage configured to store second adjustment factors associated with presentation of the second image area on the second display.

5. The interpupillary calibration system of claim 2, wherein the system further comprises an electronics pack connected to the first controller circuit and the second controller circuit, the electronics pack comprises the calibration processor, the calibration processor generating one or more first commands associated with first signals that control presentation of the first image area and one or more second commands associated with second signals that control presentation of the second image area.

6. The interpupillary calibration system of claim 5, wherein the first commands or the second commands are voice inputs or keyboard inputs, or voice inputs and keyboard inputs.

7. The interpupillary calibration system of claim 1, wherein movement of the first image area, the second image area, or first image area and the second image area comprises horizontal movement, vertical movement, or horizontal and vertical movement.

8. The interpupillary calibration system of claim 1, wherein adjustment of the display distance between the first image area and the second image area comprises size adjustment of the first image area presented on the first display, size adjustment of the second image area presented on the second display, or size adjustment of the first image and the second image.

9. The interpupillary calibration system of claim 8, wherein size adjustment of the first image area, the second image area, or first image and the second image comprises horizontal size adjustment, vertical size adjustment, or horizontal and vertical size adjustment.

10. An interpupillary calibration method for stereoscopic visualization, the interpupillary calibration method comprising:
presenting a first image area at a first position on a first display through a left aperture of an eyeframe, the first display disposed in proximity to the left aperture, the first image area associated with an image and having a first display axis;
presenting a second image area at a second position on a second display through a right aperture of the eyeframe, the second display disposed in proximity to the right aperture, the second image area associated with the image and having a second display axis; and
adjusting a display distance between the first image area and the second image area based on an interpupillary distance of a user via movement of the presentation of the first image area to a third position on the first display, movement of the presentation of the second image area to a fourth position on the second display, or movement of the first image area and the second image area respectively to the third position and the fourth position, wherein the first image area and the second image area are visible through the first aperture and the second aperture enabling formation of a stereoscopic view of the image.

11. The interpupillary calibration method of claim 10, the method further comprising:
transmitting one or more first signals from a first controller circuit to the first display to control presentation of the first image area, the first controller circuit associated with the first display; and
transmitting one or more second signals from a second controller circuit to the second display to control presentation of the second image area, the second controller circuit associated with the second display.

12. The interpupillary calibration method of claim 11, the method further comprising:
generating via a first electronic display driver the first signals to control presentation of the first image area on the first display, wherein the first controller circuit comprises the first electronic display driver; and
generating via a second electronic display driver the second signals to control presentation of the second image area on the second display, wherein the second controller circuit comprises the second electronic display driver.

13. The interpupillary calibration method of claim 12, the method further comprising:
storing first adjustment factors associated with presentation of the first image area on the first display in a first adjustment factor storage, wherein the first controller circuit comprises the first adjustment factor storage; and
storing second adjustment factors associated with presentation of the second image area on the second display in a second adjustment factor storage, wherein the second controller circuit comprises the second adjustment factor storage.

14. The interpupillary calibration method of claim 11, the method further comprising generating via a calibration processor one or more first commands associated with first signals that control presentation of the first image area and one or more second commands associated with second signals that control presentation of the second image area, wherein the calibration processor is comprised in an electronics pack that is connected to the first controller circuit and the second controller circuit.

15. The interpupillary calibration method of claim 14, the method further comprising inputting the first commands or the second commands, wherein the first commands or the second commands are voice inputs or keyboard inputs, or voice inputs and keyboard inputs.

16. The interpupillary calibration method of claim 10, wherein movement of the first image area, the second image area, or first image and the second image comprises moving the first image area, moving the second image area, or moving the first image area and the second image area horizontally, vertically, or horizontal and vertically.

17. The interpupillary calibration method of claim 10, wherein adjustment of the display distance between the first image area and the second image area comprises adjusting size of the first image area presented on the first display, adjusting size of the second image area presented on the second display, or adjusting size of the first image and the second image.

18. The interpupillary calibration method of claim 17, wherein size adjustment of the first image area, the second image area, or first image and the second image comprises horizontal size adjustment, vertical size adjustment, or horizontal and vertical size adjustment.

* * * * *